United States Patent [19]
Kohayakawa et al.

[11] Patent Number: 5,847,805
[45] Date of Patent: *Dec. 8, 1998

[54] SCAN IMAGING DEVICE FOR FORMING A STEREOSCOPIC IMAGE OF THE EYE

[75] Inventors: Yoshimi Kohayakawa, Yokohama; Kazuhiro Matsumoto, Kawasaki, both of Japan

[73] Assignee: Canon Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 820,419

[22] Filed: Mar. 26, 1997

Related U.S. Application Data

[63] Continuation of Ser. No. 272,750, Jul. 11, 1994, abandoned.

[30] Foreign Application Priority Data

Jul. 12, 1993 [JP] Japan ................................ 5-195216
Jun. 23, 1994 [JP] Japan ................................ 6-141668

[51] Int. Cl.⁶ .................................................. A61B 3/14
[52] U.S. Cl. ........................ 351/210; 351/214; 351/221
[58] Field of Search .................................. 351/205, 206, 351/210, 214, 221, 201; 356/388, 398; 354/62; 128/633, 745

[56] References Cited

U.S. PATENT DOCUMENTS

| | | | |
|---|---|---|---|
| 4,609,287 | 9/1986 | Kohayakawa | 356/124 |
| 4,697,895 | 10/1987 | Sekiguchi et al. | 351/243 |
| 4,704,012 | 11/1987 | Kohayakawa et al. | 351/211 |
| 4,768,873 | 9/1988 | Webb | 351/205 |
| 4,820,037 | 4/1989 | Kohayakawa et al. | 351/211 |
| 4,826,315 | 5/1989 | Kohayakawa | 356/125 |
| 4,830,483 | 5/1989 | Kohayakawa et al. | 351/221 |
| 4,848,896 | 7/1989 | Matsumoto | 351/211 |
| 4,952,049 | 8/1990 | Matsumoto | 351/211 |
| 4,991,953 | 2/1991 | Pflibsen et al. | 351/206 |
| 5,037,194 | 8/1991 | Kohayakawa et al. | 351/224 |
| 5,144,346 | 9/1992 | Nakamura et al. | 351/208 |
| 5,231,430 | 7/1993 | Kohayakawa | 351/243 |
| 5,231,460 | 7/1993 | Kohayakawa | 356/125 |
| 5,233,372 | 8/1993 | Matsumoto | 351/221 |
| 5,249,003 | 9/1993 | Kohayakawa | 351/211 |
| 5,280,313 | 1/1994 | Kohayakawa | 351/211 |

FOREIGN PATENT DOCUMENTS 2-84931  3/1990  Japan.

*Primary Examiner*—Huy Mai
*Attorney, Agent, or Firm*—Fitzpatrick, Cella, Harper & Scinto

[57] ABSTRACT

A scan imaging device capable of generating a stereoscopic image of an object to be examined projects two light beams and scans the object with the light beams, and the reflected light beams are obtained through the same light path and are respectively received by two light detectors for generating a set of images with a parallax. The images are displayed alternately on a television monitor and are viewed through spectacles with polarizing screens, whereby the examiner can obtain a stereoscopic view of the object.

23 Claims, 5 Drawing Sheets

SCAN IMAGING DEVICE FOR FORMING A STEREOSCOPIC IMAGE OF THE EYE

This application is a continuation of application Ser. No. 08/272,750 filed Jul. 11, 1994, now abandoned.

BACKGROUND OF THE INVENTION

1. Field of the Invention

The present invention relates to a scan imaging device for scanning an object to be examined, thereby forming an image thereof.

2. Related Background Art

The conventional scan image device such as a scanning type retinal scope scans an object to be examined while irradiating an object with a spot light beam, then receives the reflected light beam by a photoelectric sensor through a light path which is the same as that of the irradiating light beam, and converts the signal of the thus received light into an image on a television monitor, thereby providing an image with excellent resolution and contrast.

However, such a conventional device, though advantageous in providing satisfactory resolution, is incapable of providing a stereoscopic image because the reflected light beam is received by the photoelectric sensor through a light path which is the same as that of the irradiating light beam.

SUMMARY OF THE INVENTION

An object of the present invention is to solve such a problem and to provide a scan imaging device capable of stereoscopically viewing an object to be examined.

Other objects of the present invention will become fully apparent from the following description of the embodiments.

DESCRIPTION OF THE PREFERRED EMBODIMENTS

Figure 1:
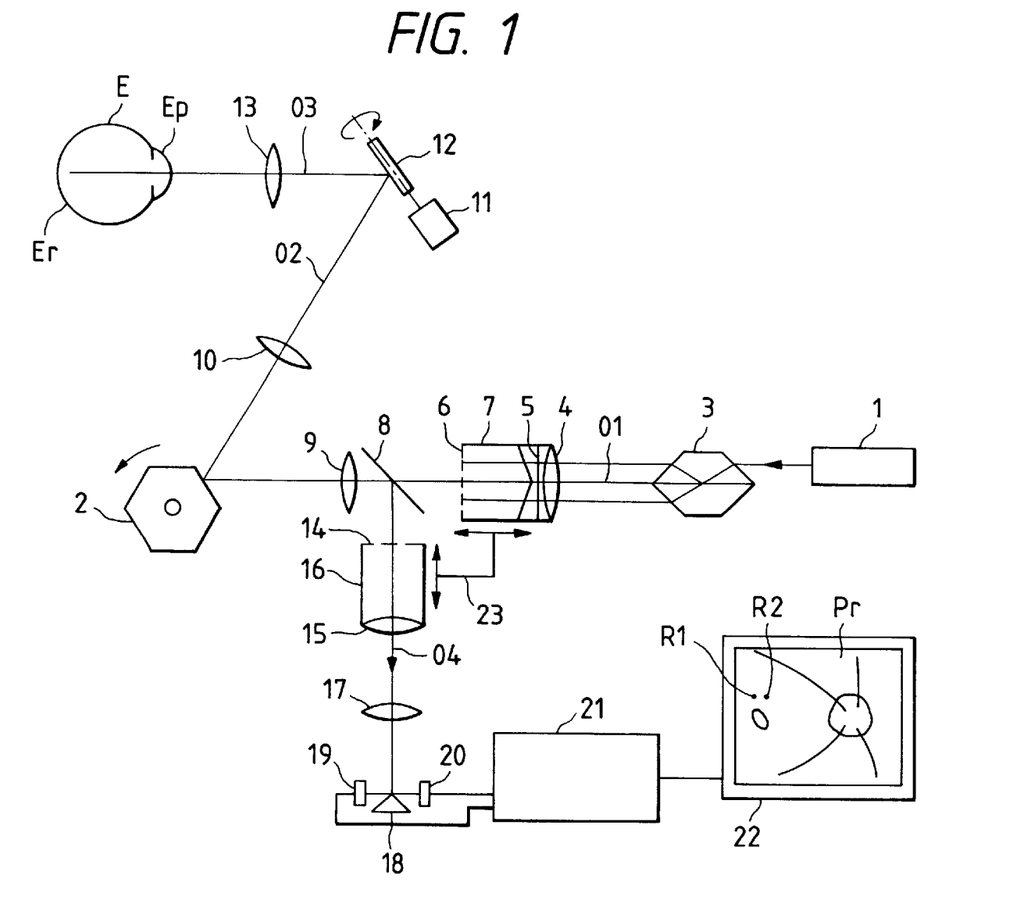
FIG. 1 is a schematic view of a first embodiment of the present invention.

FIG. 1 shows the configuration of a first embodiment of the present invention. There are provided a splitting prism 3, a focusing system 7 consisting of a focusing lens 4, a splitting prism 5 and a diaphragm 6 having two apertures, a half mirror 8 and a lens 9 on an optical path 01 from a laser light source 1 to a rotary polygon mirror 2. On an optical path 02 in the direction of reflection by the rotary polygon mirror 2 there are provided a lens 10 and a galvanometric mirror 12 rotated by rotation means 11. On an optical path 03 in the direction of reflection by the galvanometric mirror 12 there is provided a lens 13 which faces an eye E to be examined.

Also, on an optical path 04 in the direction of reflection by the half mirror 8 there are provided a focusing system 16 consisting of a diaphragm 14 having two apertures and a lens 15, a lens 17 and a splitting prism 18. Furthermore, on two optical paths in the directions of reflection of the splitting prism 18 there are respectively provided photosensors 19, 20 whose outputs are supplied to a signal processor 21 and then to a television monitor 22.

An eye fundus or retina Er and the diaphragms 6, 14 are in a mutually conjugate relationship. The diaphragms are respectively positioned on focal planes of the focusing lenses 4, 15. The focusing systems 7, 16 are linked and moved along each optical axis by a link mechanism 23. The rotary polygon mirror 2 and the galvanometric mirror 12 are in conjugation with a pupil Ep of an eye E to be examined. The rotary polygon mirror 2 has a rotary axis perpendicular to the plane of the drawing, and the galvanometric mirror 12 has a rotary axis on the drawing perpendicular to the above-mentioned rotary axis. The splitting prism 18 is positioned on the focal plane of the lens 17 and is conjugate with the retina Er of the eye E to be examined.

The light beam from the laser light source 1 is split into two light beams by the splitting prism 3. The two light beams pass through the focusing lens 4 and the splitting prism 5, are then shaped by focusing on the diaphragm 6, further pass through the half mirror 8 and the lens 9. Then, they are reflected upwards by the rotary polygon mirror 2, pass through the lens 10, then are reflected to the left by the galvanometric mirror 12, and further are introduced into the eye E to be examined through the lens 13, thus illuminating two adjacent points on the retina Er.

Figure 2:
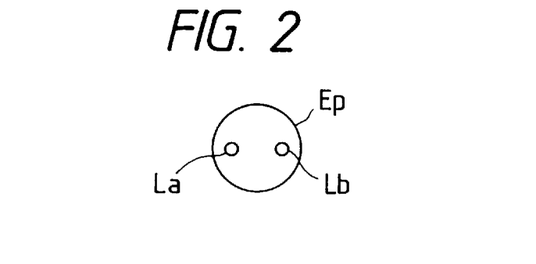
FIG. 2 is a schematic view showing irradiating and reflected light beams on the pupil, in the case in which a holed mirror is employed instead of a half mirror.

The two irradiating light beams on the retina Er, corresponding to two light beams La, Lb on the pupil Ep as shown in FIG. 2, are moved in a main scanning direction by the rotation of the rotary polygon mirror 2, and also in a sub scanning direction substantially perpendicular to the main scanning direction by the rotation of the galvanometric mirror 12.

The light beam reflected from the retina Er return through the same optical path. Then, the reflected light beams are reflected downwards by the half mirror 8, are shaped by focusing on the diaphragm 14, then are converted into parallel light beams by the lens 15, and further pass through the lens 17 and are again focused as two point images by the splitting prism 18. These images, derived respectively from the light beams reflected at different positions on the retina Er, are respectively reflected to the left and to the right by the splitting prism 18 when it is so regulated that the vertex of the splitting prism 18 is positioned at the center of the images, whereby the images are respectively received by the photosensors 19, 20 and the thus obtained photoelectric signals are inputted to the signal processor 21.

When the retina Er is scanned two-dimensionally by the rotation of the rotary polygon mirror 2 and of the galvanometric mirror 12, there can be formed from the signals of the photosensors 19, 20, two retinal images Pr observed from different directions. The two retinal images Pr are differentially polarized to alternately display them on the television monitor 22, and are observed by polarization spectacles different on left and right thereof, thereby stereoscopically observing the retinal image Pr. It is also possible to display the two retinal images Pr respectively on different television monitors to stereoscopically observe these images with the two eyes.

On the television monitor 22 in FIG. 1, there are shown positions R1, R2 of the irradiating light beams on the retina Er at a given moment. The deviation between the two points may be in the horizontal or in the vertical direction.

When the retinal images Pr are focused, the link mechanism 23 is driven, then the focusing systems 7, 16 are cooperatively moved along each optical axis, whereby the diaphragms 6, 14 are made conjugate with the retina Er through the focusing lens 4 and the lens 15, thereby focusing the retinal image Pr.

This embodiment employs the half mirror 8 for separating the irradiating light projected to the retina Er from the light beams reflected therefrom, but the half mirror 8 may be replaced by a holed mirror provided close to a position conjugate with the pupil Ep. In such a case, the two irradiating light beams pass the apertures of the holed mirror, and are projected onto two points on the retina Er from two positions in the pupil Ep. The reflected light beams are taken from the entire pupil Ep, and are reflected toward the optical path 04 by the mirror portion of the holed mirror. The diaphragm 6 having two apertures (the irradiating side) may be dispensed with.

Figure 3:
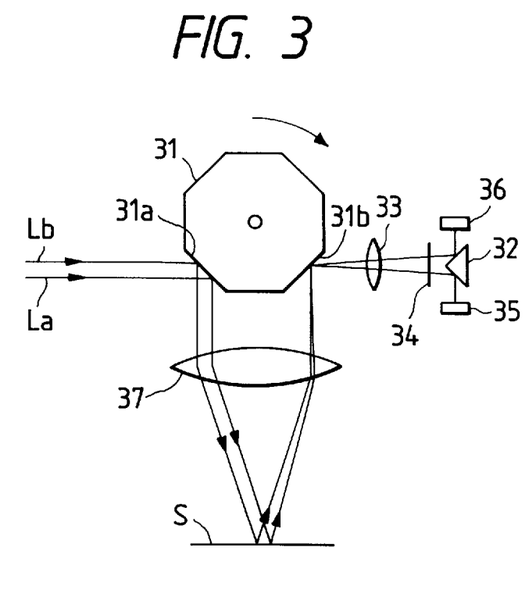
FIG. 3 is a view of a scanning optical system in a second embodiment of the present invention.

FIG. 3 shows the configuration of a second embodiment of the present invention, which is applied to a scanning type retinal scope for observing a stroma of the cornea. There are provided a condenser lens 33 and a diaphragm 34 having two apertures on an optical path from a rotary polygon mirror 31 having eight reflecting faces to a splitting prism 32. On two optical paths in the direction of reflection by the splitting prism 32 there are respectively provided photosensors 35, 36. Also, on an optical path in the direction of reflection by the rotary polygon mirror 31 there is provided an objective lens 37. The diaphragm 34 is positioned on the focal plane of the condenser lens 33.

Two irradiating light beams La, Lb from an unrepresented light source enter a first reflecting face 31a of the rotary polygon mirror 31 from the left side, thus reflected downwards and transmitted through the left-hand portion of the objective lens 37, and then are projected onto two different points of an object S to be examined. When the rotary polygon mirror 31 is rotated, the irradiating light beams La, Lb are travelled right and left to scan the object S. The reflected light beams therefrom are transmitted through a right-hand portion of the objective lens 37, then are reflected by a second reflecting face 31b of the rotary polygon mirror 31, perpendicular to the first reflecting face 31a, are further transmitted by the condenser lens 33 and are focused on the diaphragm 34. The two reflected light beams are respectively reflected in different directions by the splitting prism 32 and are received by the photosensors 35, 36. Two one-dimensional images which cause parallax can be generated on the basis of the photoelectric signals of the photosensors 35, 36, and therefore, the object S can be stereoscopically observed.

The two irradiating light beams La, Lb are fine light beams such as a laser beam, and the vertical deviation thereof generates the lateral deviation in the reflecting positions on the object S. The beam-shaped two irradiating light beams may be replaced by two irradiating light beams spreading in the object S within a plane perpendicular to the plane of the drawing. In such a case the diaphragm 34 is replaced by a slit diaphragm having two slits, and two one-dimensional CCDs are to be arranged in the same direction as that of the slits in order to receive the reflected light beams, coming from the object S and focused on the slit diaphragm. Since a one-dimensional image can be obtained from the photoelectric signal of each of the two one-dimensional CCDs, a two-dimensional image can be prepared by scanning the object S through the rotation of the rotary polygon mirror 31.

Figure 4:
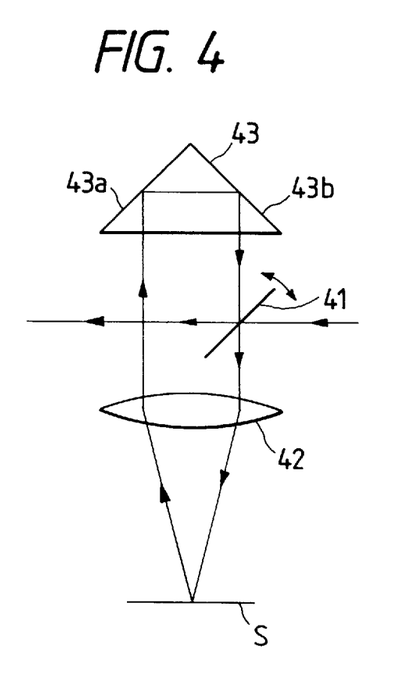
FIG. 4 is a view of a variation of the scanning optical system.

FIG. 4 shows a variation of the scanning system, in which the rotary polygon mirror 31 is replaced by a galvanometric mirror 41 for effecting the scanning operation. Below the galvanometric mirror 41 there is provided the object S through the objective lens 42. Above the mirror 41, there is provided a prism 43 having reflecting faces 43a, 43b.

The projection light beams entering the galvanometric mirror 41 from the right are reflected downwards by the mirror 41, are then transmitted by a right-hand portion of the objective lens 42, and are projected onto two different points of the object S. The reflected light beams therefrom are transmitted by a left-hand portion of the objective lens 42, are then reflected by the reflecting faces 43a, 43b of the prism 43, are introduced into the galvanometric mirror 41 from above for reflection toward the left, and are received by unrepresented photosensors.

Even if the galvanometric mirror 41 is rotated within the plane of the drawing, the projection light beams are scanned in the right and left directions, but the incident angle of the reflected light beams on the photosensors remains constant. Thus, in case of projecting two light beams onto the object S, a diaphragm with two apertures may be provided in a position, conjugate with the object S, in the receiving optical system, whereby the reflected light beams from the object S can be separated and received by photosensors provided in two directions.

Figure 5:
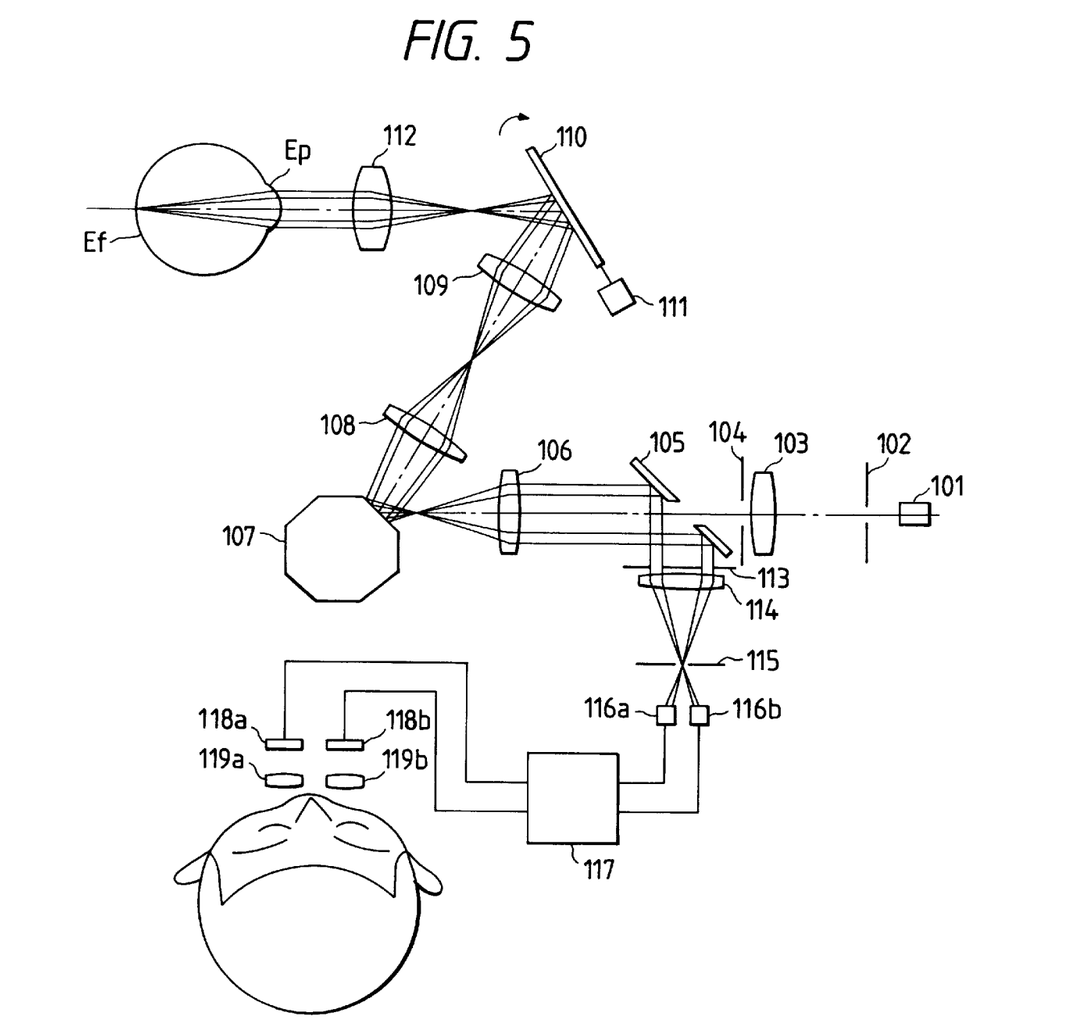
FIG. 5 is a view showing a configuration of the second embodiment.
Figure 6:
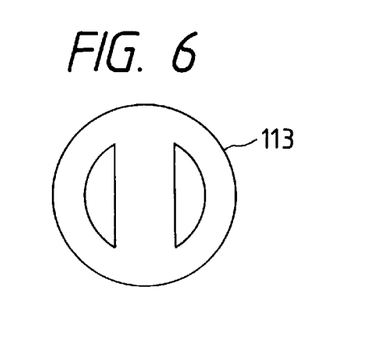
FIG. 6 is a view showing apertures of a diaphragm 113.

FIG. 5 illustrates a third embodiment of the present invention, wherein provided are a laser light source 101; a slit aperture 102; a relay lens 103; a diaphragm 104 for limiting the light beam; a holed mirror 105 having an aperture in the center portion; a relay lens 106; a rotary polygon mirror 107; relay lenses 108, 109; a galvanometric mirror 110; rotation means 111 for rotating said the galvanometric mirror; and an objective lens 112. There are further provided a diaphragm 113 having two apertures as shown in FIG. 4, for obtaining two light beams from different areas on the pupil; a pinhole 115; photosensors 116a, 116b; a signal processor 117; image display means 118a, 118b; and finder lenses 119a, 119b. There are also shown an eye fundus Ef and a pupil Ep of an eye to be examined.

The diaphragms 104, 113, rotary polygon mirror 107 and galvanometric mirror 110 are positioned in a a conjugate relationship with the pupil of the eye to be examined. The rotary polygon mirror 106 scans the light beam in the horizontal direction (main scan) and the galvanometric mirror 108 scan the light beam in the vertical direction (sub scan). The slit aperture 102 and the pinhole 115 are made conjugate with the eye fundus of the eye to be examined, and the slit aperture 102 is elongated in the main scanning direction. The apertures of the diaphragm 113 and the photosensors 116a, 116b are arranged in the main scanning direction and deviate from each other across the optical axis.

In the above-explained configuration, the light beam emitted from the laser light source 101 illuminates the slit of the slit aperture 102. The slit image thus illuminated is transmitted through the lens 103, the aperture of the diaphragm 104, the aperture of the holed mirror 105 and the lens 106, then are main-scanned in the horizontal direction by the rotary polygon mirror 107, and is further transmitted by the lenses 108, 109, and then sub-scanned in the vertical direction by the galvanometric mirror 110, and then is transmitted by the objective lens 112, and is focused as a slit on the eye fundus Ef through the pupil Ep. The slit image scans the eye fundus two-dimensionally. The reflected light beam from the thus illuminated eye fundus is transmitted through the pupil Ep and the objective lens 112, is then reflected by the galvanometric mirror 110, is further transmitted by the lenses 109, 108, is then reflected by the rotary polygon mirror 107, is transmitted by the lens 106, reflected downwards by the peripheral portion of the holed mirror 105, is and is split into two light beams at the left and the right by passing the apertures of the diaphragm 113. Thus, split two light beams pass through the lens 113 and the pinhole 115 and reach the respectively corresponding photosensors 116a, 116b. The light reaching the photosensors 116a, 116b are converted into electrical signals and are supplied to the signal processor 117. The outputs of the photosensors 116a, 116b, obtained by the scanning of the eye fundus, are converted into a set of video signals at the left and the right, which are respectively displayed on the image display means 118a, 118b. An examiner observes the eye fundus images displayed on the image display means 118a, 118b, respectively with the left and right eyes, through the finder lenses 119a, 119b. Since the images are obtained by observation of the eye fundus with a parallax from different directions on the pupil of the eye, the examiner can stereoscopically observe the eye fundus.

Figure 7:
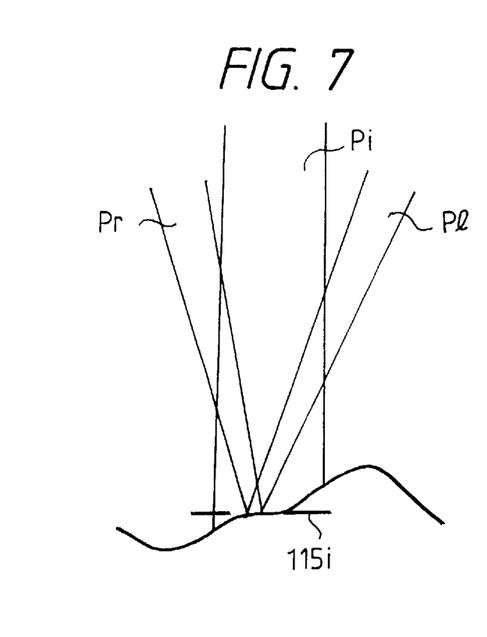
FIGS. 7 to 9 are views showing the principle of stereoscopic observation.
Figure 8:
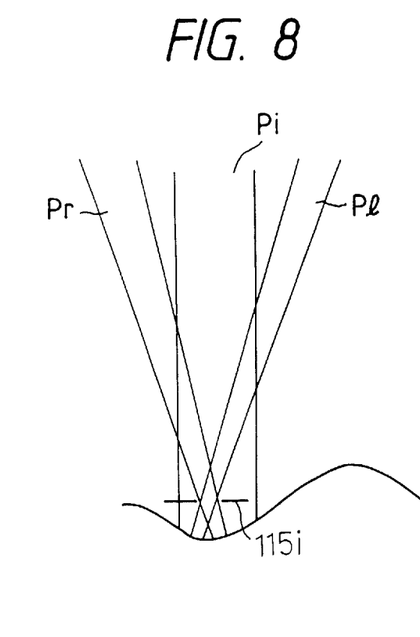
Figure 9:
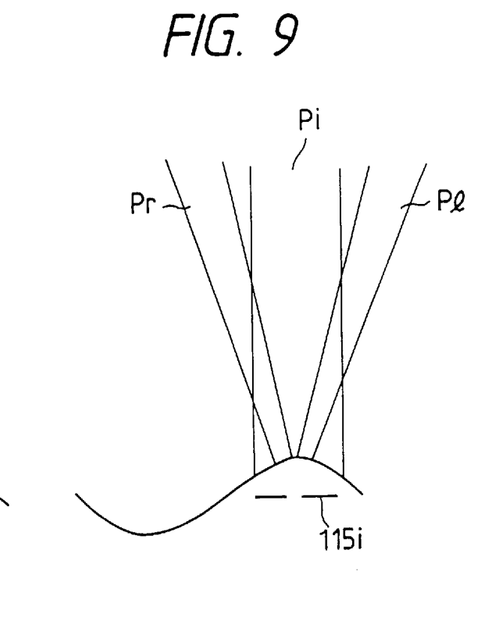
Figure 10:
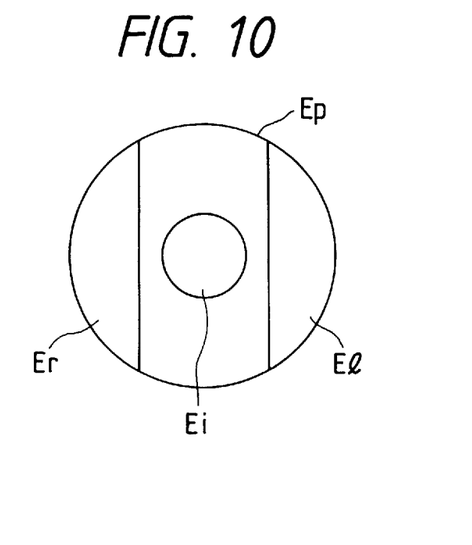
FIG. 10 is a view showing the state of separation of light beams on the pupil.

Below there will be explained the principle of the stereoscopic observation with reference to FIGS. 7 to 10. FIGS. 7 to 9 show the state of entering and emerging of the light beams at the eye fundus. FIG. 10 shows the cross section of the light beams at the pupil. In FIG. 10 there are shown a pupil Ep of the eye to be examined, an entrance area Ei for the eye fundus irradiating light; and emerging areas Er, El of the reflected light beams from the eye fundus. In FIGS. 7 to 9, there are shown a light beam Pi illuminating the eye fundus from the area Ei; an image 115i of the pinhole 115 projected onto the eye fundus; a reflected light beam Pr passing through the pupil area Er and the pinhole 115; and a reflected light beam Pl passing through the pupil area El and the pinhole 115. FIGS. 7 to 9 illustrate different moments of scanning of an eye fundus area with surface irregularity. FIG. 7 shows a state in which the plane 115i of the image of the pinhole 115 coincides with the eye fundus, while FIG. 8 shows a state in which the eye fundus is positioned behind the pinhole image plane, and FIG. 9 shows a state in which the eye fundus is positioned in front of the image plane. When the eye fundus coincides with the image plane of the pinhole 115 as shown in FIG. 7, the reflected light beams Pr, Pl come from the same area of the eye fundus, so that the photosensor 116a, 116b receive the reflected light beams from the same area of the eye fundus. On the other hand, if the eye fundus is positioned behind or in front of the image plane of the pinhole 115 as shown in FIGS. 8 and 9, the light beams Pr, Pl come from different areas of the eye fundus, so that the photosensors 116a, 116b receive signals of different intensities. Consequently, there is produced a parallax in the image signals generated from these signals in the signal processor 117. The examiner can achieve stereoscopic observation by looking at these images with the left and right eyes. Such images of different intensities, namely including a parallax can be obtained by making the area to be light-received on the eye fundus smaller than the illuminated area by means of the pinhole 115.

Figure 11:
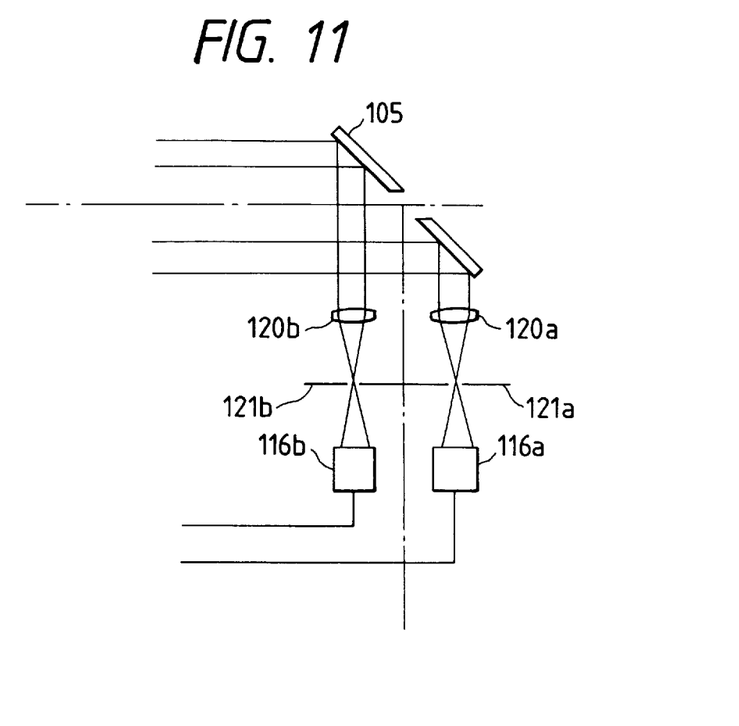
FIG. 11 is a view showing the arrangement of pinholes, lenses and photosensors in a fourth embodiment of the present invention.

In the foregoing embodiment, the photosensors 116a, 116b are positioned behind the pinhole 115, but it is also possible, as shown in FIG. 11, to receive the reflected light beams at the left and the right by the photosensors 116a, 116b independently through lenses 120a, 120b which are made substantially conjugate with the pupil, and pinholes 121a, 121b which are made substantially conjugate with the eye fundus. Such a configuration will facilitate the positioning of the photosensors 116a, 116b.

Also, if the light-receiving faces of the photosensors are sufficiently small, such light-receiving faces can substantially serve as the pinholes if the photosensors are positioned on a plane substantially conjugate with the eye fundus. In such case, the pinhole 121a, 121b can be dispensed with.

What is claimed is:

1. A scan imaging device comprising:

a light projecting system for protecting two light beams onto different portions of an object through a scanning optical system and simultaneously scanning the object with the two light beams;

a light receiving system having light splitting means for splitting two reflected light beams, reflected from the object through said scanning optical system and directing the two reflected light beams to two light detectors, said light splitting means being located immediately in front of the two light detectors an output unit for forming a stereoscopic image of the object by signals from said two light detectors.

2. A device according to claim 1, wherein said scanning optical system includes a rotary reflecting member for simultaneously angularly deflecting the two light beams.

3. A device according to claim 2, wherein said rotary reflecting member is adapted to simultaneously angularly deflect two reflected light beams coming from the inspected object scanned with the two projected light beams and respectively corresponding to the two projected light beams.

4. A device according to claim 3, wherein said rotary reflecting member is a rotary polygon mirror.

5. A device according to claim 3, wherein said rotary reflecting member is a galvanometric mirror.

6. A device according to claim 1, wherein said scanning optical system is adapted to two-dimensionally scan the object with the two light beams.

7. A device according to claim 1, wherein said scanning optical system is adapted to one-dimensionally scan the object with two slit-shaped light beams, and wherein said two light detectors are composed of a one-dimensional charge coupled device.

8. A device according to claim 1, wherein said output unit includes a television monitor.

9. A device according to claim 8, wherein said television monitor is adapted to display, alternately, images obtained respectively from the outputs of said two light detectors.

10. A device according to claim 1, wherein said scanning optical system is adapted to scan the inspected object with two light beams, and said device further comprises a link mechanism for linking the focusing of the two light beams onto the object and the focusing of the two reflected light beams onto said two light detectors.

11. A device according to claim 1, wherein said light splitting means comprises a prism.

12. A device according to claim 1, wherein said light splitting means directs the two reflected light beams directly to the two light detectors without the two reflected light beams passing through any other optical element.

13. A scan imaging device comprising:

a light projecting system for projecting two light beams onto different portions of an eye to be examined through a scanning optical system and simultaneously scanning the eye with the two light beams;

a light receiving system having light splitting means for splitting two reflected light beams, reflected from the eye through said scanning optical system and directing the two reflected light beams to two light detectors, said light splitting means being located immediately in front of the two light detectors; and an output unit for forming a stereoscopic image of the eye by signals from said two light detectors.

14. A device according to claim 13, wherein said scanning optical system includes a rotary reflecting member for simultaneously angularly deflecting the two light beams.

15. A device according to claim 14, wherein said rotary reflecting member is adapted to simultaneously angularly deflect two reflected light beams coming from the eye scanned with the two projected light beams and respectively corresponding to the two projected light beams.

16. A device according to claim 13, wherein said scanning optical system is adapted to scan an eye fundus of the eye with the two light beams.

17. A device according to claim 13, wherein said light splitting means comprises a prism.

18. A device according to claim 13, wherein said light splitting means directs the two reflected light beams directly to the two light detectors without the two reflected light beams passing through any other optical element.

19. An ophthalmic scan imaging device comprising:

an optical system including a scanning optical system for projecting a light beam onto an eye to be examined and scanning the eye with said light beam, separation means for separating a light beam, emerging from the eye and obtained through said scanning optical system, into two areas in the cross section of the light beam at a position conjugate with a pupil of the eye, and diaphragm means for limiting the two light beams emerging from said separation means, at a position conjugate with the scanned position of the eye;

two light detectors for respectively receiving the two reflected light beams from the inspected eye, obtained through said scanning optical system, separated by said separation means and limited by said diaphragm means simultaneously; and an output unit for forming a stereoscopic image of the eye by signals of said two light detectors.

20. A device according to claim 19, wherein said diaphragm means is adapted to made the area on the scanned position of the eye, to be subjected to light reception by said light detectors, smaller than the illumination area by the scanning optical system.

21. A device according to claim 19, wherein said diaphragm means is provided with two apertures corresponding to said two light detectors, respectively.

22. An ophthalmic apparatus comprising:

a scanning optical system for projecting one light beam onto an eye to be examined and scanning the eye with the light beam;

a beam separation member for separating a light beam, emerging from an area, on which said one light beam is projected, of the eye and guided through said scanning optical system, into two areas in the cross section of the light beam at a position conjugate with a pupil of the eye;

a diaphragm member for limiting the two light beams emerging from said beam separation member, at a position conjugate with the scanned position of the eye;

two light detectors for respectively and simultaneously receiving the two light beams limited by said diaphragm member; and an output unit for forming a stereoscopic image of the eye by signals of said two light detectors.

23. An ophthalmic apparatus comprising:

a scanning optical system for projecting one light beam onto an eye to be examined and scanning the eye with the light beam;

a beam separation member for separating a light beam, emerging from an area of the eye, on which said one light beam is projected, and guided through said scanning optical system, into two areas in the cross section of the light beam at a position not conjugate with the scanned position of the eye;

a diaphragm member arranged at a position conjugate with the scanned position of the eye for substantially limiting two light beams each of which passes through a respective one of said two areas;

two light detectors for respectively receiving the two light beams limited by said diaphragm member simultaneously; and an output unit for forming a stereoscopic image of the eye by signals of said two light detectors.

* * * * *

UNITED STATES PATENT AND TRADEMARK OFFICE
CERTIFICATE OF CORRECTION

PATENT NO.    : 5,847,805

DATED         : December 8, 1998

INVENTOR(S)   : YOSHIMI KOHAYAKAWA, ET AL.

It is certified that error appears in the above-identified patent and that said Letters Patent is hereby corrected as shown below:

COLUMN 1,
Line 48, "a" (second occurrence) should read --the--, and "the" should read --a--.

COLUMN 2,
Line 45, "beam" should read --beams--.
Line 48, "then are" should read --are then--.

COLUMN 3,
Line 16, "light" (first occurrence) should read --light beams--.
Line 48, "then are" should read --are then--.
Line 66, "case" should read --case,--.

COLUMN 4,
Line 41, "said" should be deleted.
Line 50, "a a" should read --a--.
Line 54, "scan" should read --scans--.
Line 67, "are" should read --is--.

UNITED STATES PATENT AND TRADEMARK OFFICE
CERTIFICATE OF CORRECTION

PATENT NO. : 5,847,805

DATED : December 8, 1998

INVENTOR(S) : YOSHIMI KOHAYAKAWA, ET AL.

It is certified that error appears in the above-identified patent and that said Letters Patent is hereby corrected as shown below:

COLUMN 5,
Line 11, "106," should read --106, is--.
Line 13, "105, is" should read --105,--.
Line 17, "light" should read --light beams--.
Line 53, "photosensor" should read --photosensors--.

COLUMN 6,
Line 14, "pinhole" should read --pinholes--.
Line 26, "detectors" should read --detectors; and--.

COLUMN 7,
Line 31, "said" should read --the--.
Line 48, "made" should read --make--.

COLUMN 8,
Line 2, "area by the" should read --area illuminated by said--.

Signed and Sealed this

Seventh Day of September, 1999

Attest:

Q. TODD DICKINSON

Attesting Officer

Acting Commissioner of Patents and Trademarks